US012788483B2

(12) United States Patent
Moriyama et al.

(10) Patent No.: US 12,788,483 B2
(45) Date of Patent: Nov. 10, 2026

(54) SURGICAL PERFORATION BETWEEN THE AORTA AND LEFT ATRIUM

(71) Applicant: Boston Scientific Medical Device Limited, Galway (IE)

(72) Inventors: Eduardo Moriyama, Richmond (CA); Gareth Davies, Toronto (CA); Matthew DiCicco, Guelph (CA)

(73) Assignee: Boston Scientific Medical Device Limited, Galway (IE)

(*) Notice: Subject to any disclaimer, the term of this patent is extended or adjusted under 35 U.S.C. 154(b) by 683 days.

(21) Appl. No.: 18/192,369

(22) Filed: Mar. 29, 2023

(65) Prior Publication Data

US 2023/0233253 A1 Jul. 27, 2023

Related U.S. Application Data

(63) Continuation of application No. PCT/IB2021/057726, filed on Sep. 9, 2021.

(60) Provisional application No. 63/084,686, filed on Sep. 29, 2020.

(51) Int. Cl.

| | |
|---|---|
| ***A61B 18/14*** | (2006.01) |
| ***A61B 90/00*** | (2016.01) |
| *A61B 17/00* | (2006.01) |

(52) U.S. Cl.

CPC .......... *A61B 18/1492* (2013.01); *A61B 90/39* (2016.02); *A61B 2017/00022* (2013.01)

(58) Field of Classification Search

CPC ..... A61B 18/12; A61B 18/14; A61B 18/1477; A61B 18/1492; A61B 18/1487; A61B 2018/00351; A61B 2018/144; A61B 2018/00273; A61B 2018/00279; A61B 2018/00357; A61B 2018/0038; A61B 2018/00392; A61B 2018/00601; A61B 2018/1475; A61B 2017/00358; A61B 2017/00022

USPC ........ 606/32, 34, 39, 41, 42, 45, 46; 607/96, 607/98, 99, 101, 113, 115, 116, 119, 122, 607/126

See application file for complete search history.

(56) References Cited

U.S. PATENT DOCUMENTS

| | | | | |
|---|---|---|---|---|
| 2002/0123698 | A1* | 9/2002 | Garibotto | A61B 17/3417 600/585 |
| 2007/0185522 | A1 | 8/2007 | Davies et al. | |
| 2009/0287210 | A1 | 11/2009 | Kauphusman et al. | |
| 2012/0059459 | A1* | 3/2012 | Asirvatham | A61M 60/20 623/3.26 |

(Continued)

OTHER PUBLICATIONS

International Search Report for PCT Application No. PCT/IB2021/057726 mailed Nov. 24, 2021.

*Primary Examiner* — Thomas A Giuliani
(74) *Attorney, Agent, or Firm* — Nelson Mullins Riley & Scarborough LLP

(57) ABSTRACT

Apparatuses and methods are disclosed for the perforation of a communication between the aorta and left atrium. The method includes introducing the apparatus, positioning the apparatus at a location along the aorta, and energizing the apparatus to create a perforation. For example, one method may include: introducing a flexible wire into the left atrium, advancing a dilator along the flexible wire to position the flexible wire adjacent a selected location along the aorta and energizing the flexible wire to create a perforation from the left atrium into the aorta.

13 Claims, 18 Drawing Sheets

(56) References Cited

U.S. PATENT DOCUMENTS

| | | | | |
|---|---|---|---|---|
| 2016/0175009 | A1* | 6/2016 | Davies | A61B 17/3478 606/191 |
| 2019/0167197 | A1 | 6/2019 | Abunassar et al. | |
| 2020/0391016 | A1* | 12/2020 | Passman | A61F 2/2475 |
| 2020/0397472 | A1* | 12/2020 | MacDonald | A61M 60/109 |
| 2023/0233254 | A1* | 7/2023 | Moriyama | A61M 25/0082 606/41 |

* cited by examiner

SURGICAL PERFORATION BETWEEN THE AORTA AND LEFT ATRIUM

CROSS-REFERENCE TO RELATED APPLICATIONS

This application is a continuation of and claims the benefit of International Application Number PCT/IB2021/057726, entitled "SURGICAL PERFORATION BETWEEN THE AORTA AND LEFT ATRIUM," and filed Sep. 9, 2021, which claims the benefit of U.S. Provisional Application No. 63/084,686, entitled "SURGICAL PERFORATION BETWEEN THE AORTA AND LEFT ATRIUM," and filed Sep. 29, 2020, which are hereby incorporated by reference in their entireties.

FIELD

This disclosure relates to surgical perforation between the aorta and left atrium. More specifically, this disclosure relates to the use of a flexible wire and a dilator to percutaneously introduce and position the flexible wire against the aorta and cause the flexible wire to create a perforation between the aorta and the left atrium.

BRIEF DESCRIPTION OF THE DRAWINGS

In order that the invention may be readily understood, embodiments of the invention are illustrated by way of examples in the accompanying drawings, in which.

DETAILED DESCRIPTION

Figure 1:
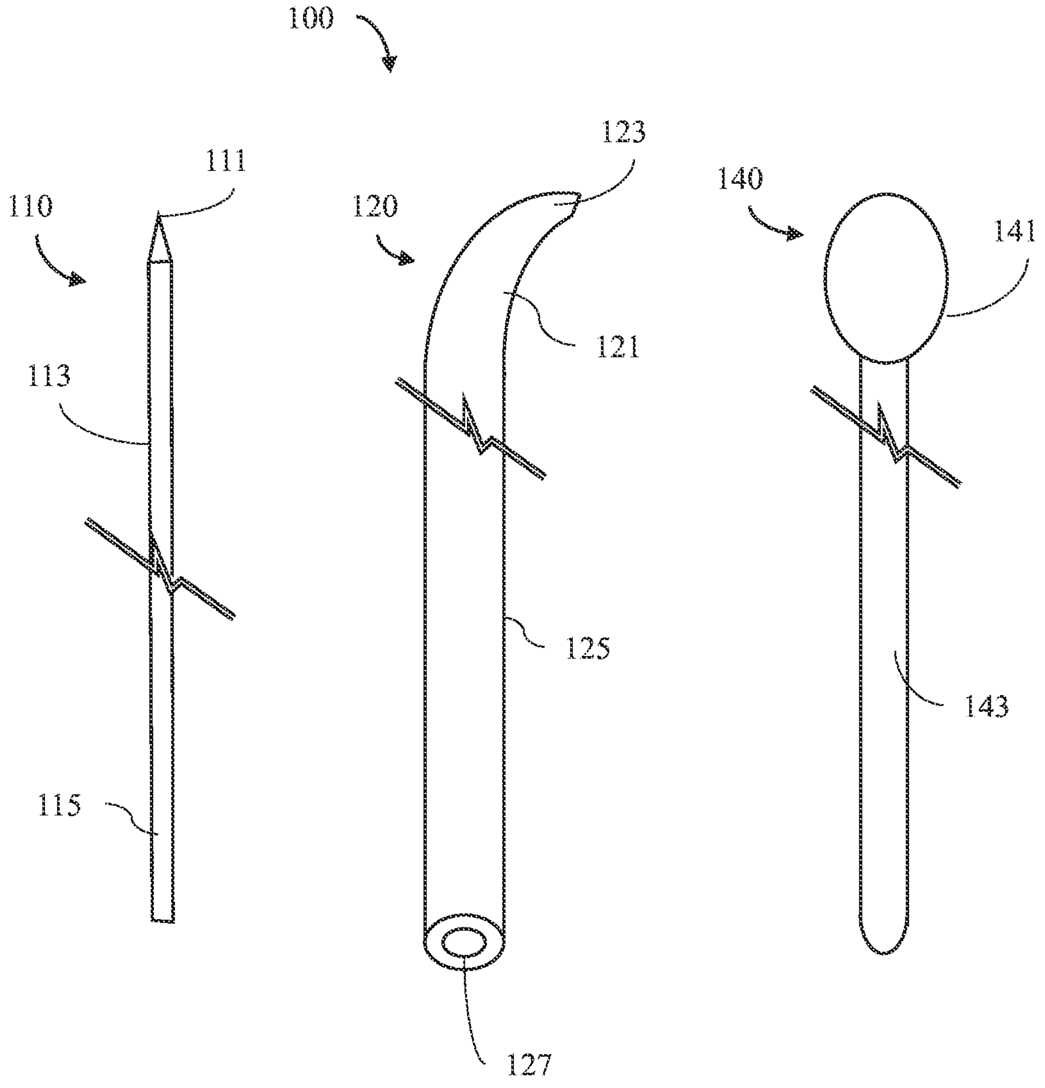
FIG. 1 is an illustration of a system in accordance with an embodiment.

With specific reference now to the drawings in detail, it is stressed that the particulars shown are by way of example and for purposes of illustrative discussion of certain embodiments of the present invention only. Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

It is often necessary to create perforations between various chambers of the heart and surrounding central vasculature to study etiology, pressure gradients, or enable end-therapy. For example, a left ventricular assist device ("LVAD") may be used in a heart failure patient to provide sufficient blood flow to peripheral organs, keeping the patient alive as a bridge to transplantation or engendering return of native heart function. Percutaneous catheter LVAD support through connection of the left atrium to the aorta may be used as a bridge to recovery in heart failure patients specifically because it is non-invasive to ventricular muscle. Conventionally, this is achieved by tracking an LVAD catheter from the left atrium, through the mitral valve, to the left ventricle and then through the aortic valve into the aorta. Certain limitations may be associated with this conventional method, such as effusions, valve stenosis, hematoma, and vessel dissection.

In one aspect, there is a need to create a direct perforation between the aorta and the left atrium. In another aspect, there is a need to create a perforation between the aorta and left atrium while avoiding the mitral and aortic valves and the left ventricle.

The present disclosure provides a system for creating a perforation from the left atrium to the aorta. In another embodiment, the present disclosure provides a method for creating a perforation from the left atrium to the aorta. In still another embodiment, the present disclosure provides for the use of a dilator and a flexible wire to create a perforation from the left atrium to the aorta. In yet another embodiment, the present disclosure provides for a kit for creating a perforation from the aorta to the left atrium.

In one embodiment, a system according to this disclosure comprises a flexible wire capable of navigating a patient's vasculature and, when energized inside the patient's aorta or left atrium, creating a perforation between the patient's aorta and left atrium. The system further comprises a dilator having at least one open lumen for receiving the flexible wire and having, or capable of being foamed to have, a curvature for directing the flexible wire into position for creating the perforation.

In another embodiment, the system comprises a flexible wire having a proximate section and a distal section terminating in an atraumatic anchor at its operative distal tip. The anchor may retain the operative distal tip of the flexible wire in position within a patient's heart so that a therapy device may be advanced along the flexible wire into position through a perforation between the aorta and left atrium.

In at least one embodiment, the flexible wire is a radio frequency ("RF") wire that, when energized against tissue of a patient's heart, creates a perforation. In another embodiment, the flexible wire is a Bovie™ mechanical guidewire, or a flexible or steerable needle, or a mechanical wire that, when mechanically energized against tissue of a patient's heart, creates a perforation.

According to one or more embodiments, the dilator is a steerable dilator having a steerable curvature to direct the flexible wire into position against tissue of the patient's heart to create at least the perforation between the aorta and the left atrium of a patient's heart. The dilator comprises a tapered tip to widen a perforation created by the flexible wire. The dilator is suitably stiff so that it can be pushed into the perforation during widening, while the distal tip of the dilator is steerable to facilitate positioning within the patient's heart. For example, the dilator may be made of high-density polyethylene, low-density polyethylene, or other suitable braided or non-braided material. The dilator preferably has a French size between 8.8 F and 24 F. The dilator may be used in conjunction with a sheath so that the perforation is retained. The dilator may comprise multiple components or the dilator may have a unibody construction. The dilator may comprise a steering mechanism, such as a steering ring or push rod mechanism configured to deflect the distal tip. Steering may be uni-directional bi-directional.

In one or more embodiments, a method according to this disclosure comprises directing an operative distal tip of a flexible wire through a patient's vasculature into the left atrium of a patient's heart toward a target location to be perforated. The method further comprises advancing a steerable dilator along the flexible wire to direct the operative distal tip adjacent the target location along the ascending aorta and energizing the operative distal tip to create a perforation into the aorta. The method may further comprise: enlarging the perforation by advancing the steerable dilator into the ascending aorta through the perforation; withdrawing the steerable dilator from the perforation; and advancing a therapeutic device over the flexible wire into position through the perforation between the aorta and left atrium. The dilator may be selected to enlarge the perforation sufficiently to accommodate the therapeutic device.

In other embodiments of the present disclosure, the method comprises: introducing a flexible wire and a dilator through a patient's vasculature into the ascending aorta of the patient's heart toward a target location opposite the left atrium; advancing the dilator along the flexible wire to position the operative distal tip of the flexible wire against the target location along the wall of the aorta, and energizing the flexible wire to create a perforation at the target location through the wall and into the left atrium. The method may further comprise: advancing the dilator along the flexible wire through the perforation to enlarge the perforation; withdrawing the dilator; engaging the operative distal tip of the flexible wire using the snare of a lasso catheter disposed in plane with the operative distal tip of the flexible wire in the left atrium; flossing the flexible wire using the lasso catheter; replacing the flexible wire with a more rigid wire; and advancing a therapeutic device through the patient's vasculature along the flexible wire or more rigid replacement wire; and positioning the therapeutic device into position between the aorta and left atrium through the perforation.

In at least one embodiment, a method of creating a perforation between the aorta and left atrium of a patient's heart comprises: introducing the operative distal tip of a flexible wire through a patient's vasculature into the right atrium of the heart; advancing a steerable dilator along the flexible wire to position the operative distal tip against the atrial septum of the heart; energizing the flexible wire to create a perforation from the right atrium into the left atrium; advancing the operative distal tip into the left atrium; advancing the steerable dilator along the flexible wire to position the operative distal tip against the wall of the ascending aorta; energizing the flexible wire to create a perforation from the left atrium into the ascending aorta; advancing the operative distal tip through the snare or a lasso catheter disposed in plane within the aorta; engaging the operative distal tip with the snare; advancing the steerable dilator along, the flexible wire to enlarge the perforation; withdrawing the steerable dilator; and advancing a therapeutic device along the flexible wire into position through the perforation between the left atrium and the aorta.

In some embodiments, a method of creating a perforation between the aorta and left atrium of a patient's heart comprises: introducing the operative distal tip of a flexible wire through a patient's vasculature into the aorta; advancing a steerable dilator along the flexible wire to position the operative distal tip against the wall of the aorta opposite the left atrium; energizing the flexible wire to create a perforation from the aorta into the left atrium; advancing the operative distal tip into the left atrium; advancing the steerable dilator along the flexible wire to position the operative distal tip against the transatrial septum; energizing the flexible wire to create a perforation from the left atrium into the right atrium; advancing the operative distal tip through the snare of a lasso catheter disposed in plane within the right atrium; engaging the operative distal tip with the snare; advancing the steerable dilator along the flexible wire to enlarge the perforation; withdrawing the steerable dilator; and advancing a therapeutic device along the flexible wire into position through the perforation between the left atrium and the aorta.

Some embodiments comprise visualization or pressure-sensing systems and methods to gauge adequate placement of a flexible wire, dilator, lasso catheter and therapeutic devices within a patient's heart.

In at least one embodiment, the operative distal tip of the flexible wire is equipped with a pressure sensor to detect pressure differentials between the left atrium and aorta. In another embodiment, the flexible wire and the dilator comprise one or more visualization markers to assist in positioning the flexible wire and the dilator during a procedure to create a perforation between the aorta and the left atrium.

Access to a patient's heart may be obtained from arterial or venous vasculature. For example, access may be obtained from venous vasculature using an inferior approach, that is, from the femoral vein through the inferior vena cava. Alternatively, access may be obtained from venous vasculature using a superior approach (for example, when an inferior approach is contraindicated as described in US20200147360 which is entirely incorporated by reference into this disclosure) by approaching from the jugular vein through the superior vena, cava. An arterial approach via, for example, a patient's femoral artery may also provide access to a patient's heart. Arterial access through the left or right femoral artery) may be provided using any suitable technique, such the Seldinger technique or transcaval technique.

FIG. 1 illustrates an embodiment of a system 100 for creating a perforation between the aorta and left atrium of a patient's heart. System 100 comprises a flexible wire 110, a dilator 120 and, optionally, a lasso catheter 140.

In at least one embodiment, the flexible wire 110, the dilator 120 and, optionally, the lasso catheter 140, are provided in a kit form.

The flexible wire 110 has a proximal section 115 and a distal section 113 terminating at an operative distal tip 111. The flexible wire 110 is adapted to be inserted within a patient's vasculature and manoeuvred to a desired position within the patient's heart for creating a perforation. The flexible wire 110 may be any wire suitable for creating a perforation, such as an RF wire, and sufficiently flexible to negotiate the tortuous anatomy of the vasculature selected for navigating the distal section 113 into the patient's heart. For example, the flexible wire may be an RF wire, such as the fly Nykanen™ wire or VersaCross® RF wire provided by Baylis Medical Company Inc. of Mississauga, Ontario, Canada, L4W 5S4. Alternatively, the flexible wire 110 may be a mechanical puncture wire, or a flexible or steerable needle having sufficient flexibility to navigate the tortuous anatomy encountered during percutaneous access through a patient's vasculature to the heart. For example, the NRG™ transseptal needle may be suitable for this purpose. The guidewire or needle may be energized to facilitate creation of the perforation.

In one embodiment, the distal section 113 of the flexible wire 110 may comprise an anchoring element to support the placement of therapy devices once the flexible wire is positioned in a patient's heart, without the need for flossing the flexible wire 110. For example, the flexible wire may have a "J" tip or a pigtail distal section similar to the distal section of the ProTrack™, VersaCross® or SupraCross® wires provided by Baylis Medical Company Inc. In embodiments where the flexible wire has a pigtail distal section, the distal section of the flexible wire has a shape memory such that, when received within the lumen of the dilator, it conforms to the curvature of the dilator but curves back into the pigtail form where it extends from the distal tip of the dilator. The pigtail shape is sufficiently stiff to provide anchorage from the exit side of a perforation so that the flexible wire is prevented from inadvertently retracting through the perforation. A suitable pigtail shape may permit tracking along the flexible wire without the need for flossing.

In the particular illustrated embodiment, the flexible wire 110 is an RF wire having an atraumatic operative distal tip and floppy distal section 113. For example, the operative distal tip 111 may be blunt to prevent inadvertent mechanical perforation. The distal section may incorporate a pre-formed, angled or straight profile. The operative distal tip 111 of the flexible wire is comprised of an electrode configured to perforate heart tissue when energized. The flexible wire may further have a main body with a stiffness that is similar to or greater than suitable exchange wires, permitting the flexible wire to also function as a support guidewire. The flexible wire may be sufficiently flexible to facilitate advancement through the curved lumen of the dilator and may support sheath, and, once it exits the lumen, sufficiently stiff to facilitate tracking of any device while in position within the heart. For example, if the flexible wire 110 has a pigtail distal section, the distal section 113 may be more flexible than the rest of the flexible wire 110. If an RF wire, the flexible wire may be insulated to facilitate transmission of RE energy when the RE wire is energized.

The steerable dilator 120 may be a large bore dilator, that is, a dilator having an outer diameter corresponding to a French size of 14 F or greater, or preferably 18 F. The dilator 120 may have an atraumatic distal tip 123, and at least one open lumen 127 for receiving the flexible wire 110, as shown in greater detail in FIG. 2. The dilator 120 also may comprise one or more visualization markers, such as such as radiopaque ("RO") markers, electro-anatomical mapping ("EAM") markers, or echogenic markers or features along at least the distal section 121 to aid in placement. The dilator 120 may be combined with a sheath.

At least the distal section 121 of the dilator has a steerable curvature that can be adjusted to direct placement of the flexible wire 110 within a patient's heart. The dilator 120 comprises a steering mechanism disposed at the proximal section. The steerable dilator may be adapted for uni- or bi-directional or single- or multi-plane steerability. For example, some embodiments may use a uni-directional steerable dilator if the direction of deflection is known ahead of the procedure such that a bi-directional dilator is not required. The steerable dilator may also present a curve while its distal section 121 is steerable. Accordingly, the steerable dilator may also comprise a metal tube, such as a hypotube, along some or all of its length that may permit the curvature to be adjusted prior to insertion into a patient. For example, the section of the dilator comprised of the hypotube may be adjusted prior to introduction into the patient while the distal section 121 is steerable.

A hemostatic valve to prevent blood loss may be provided at the proximal section of the steerable dilator.

In at least one embodiment, the system 100 comprises a lasso catheter 140 having, a snare 141 for retaining the operative distal tip 111 of the flexible wire 110. The lasso catheter 140 may permit flossing of the flexible wire 110 or retain the flexible wire 110 in position so that therapeutic devices can be advanced along the flexible wire 110.

To enable visualization, as described below, one or both of the flexible wire 110 and dilator 120 may also comprise one or more markers for visualization to aid in placement, such as RO markers EAM markers, or echogenic markers or features. The flexible wire 110 may further comprise a pressure sensor configured to measure pressure so that access to a patient's aorta or left atrium can be determined based on pressure differentials.

Embodiments of the present disclosure provide a method of percutaneous surgical perforation of a communication between the aorta and the left atrium. The method may typically involve at least the following steps: introducing a flexible wire into the left atrium toward a target location, advancing a steerable dilator along the flexible to position the flexible wire adjacent the target location on the wall of the aorta, and energizing the flexible wire to create a perforation through the wall from the left atrium into the aorta. Specific details of an example implementation are discussed below.

Figure 3A:
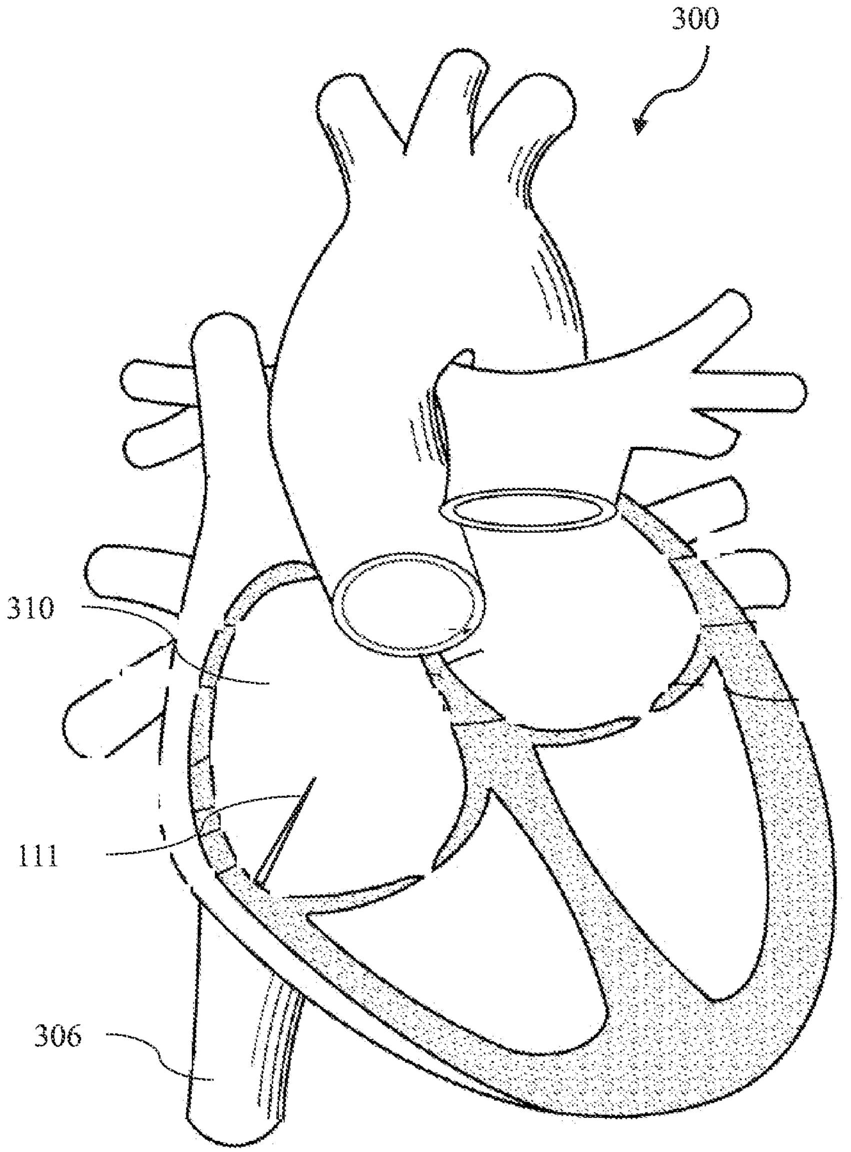
FIGS. 3A-3H illustrate an embodiment of a method to surgically create a perforation from the aorta to the left atrium of a patient's heart.

As one specific example of this method, operational steps for a method of creating a transseptal perforation according to the embodiments of this disclosure are outlined in FIGS. 3A to 3G. In accordance with a method aspect of this disclosure for creating a perforation from the left atrium into the aorta, the flexible wire may be advanced into the right atrium 310, as shown in FIG. 3A. The operative distal tip 111 of flexible wire 110 may be introduced into the patient's vasculature to reach the right atrium 310 of the patient's heart 300. Access to the right atrium 310 may be made via the inferior vena cava ("IVC") 306, as shown in FIG. 3, or via the superior vena cava ("SVC"). In accordance with the illustrated embodiment, access to the vasculature may be gained via the femoral vein. However, it will be appreciated that access to the vasculature may be achieved through a variety of pathways which are capable of accommodating the flexible wire and dilator and the present invention is not limited in this regard.

Figure 3B:
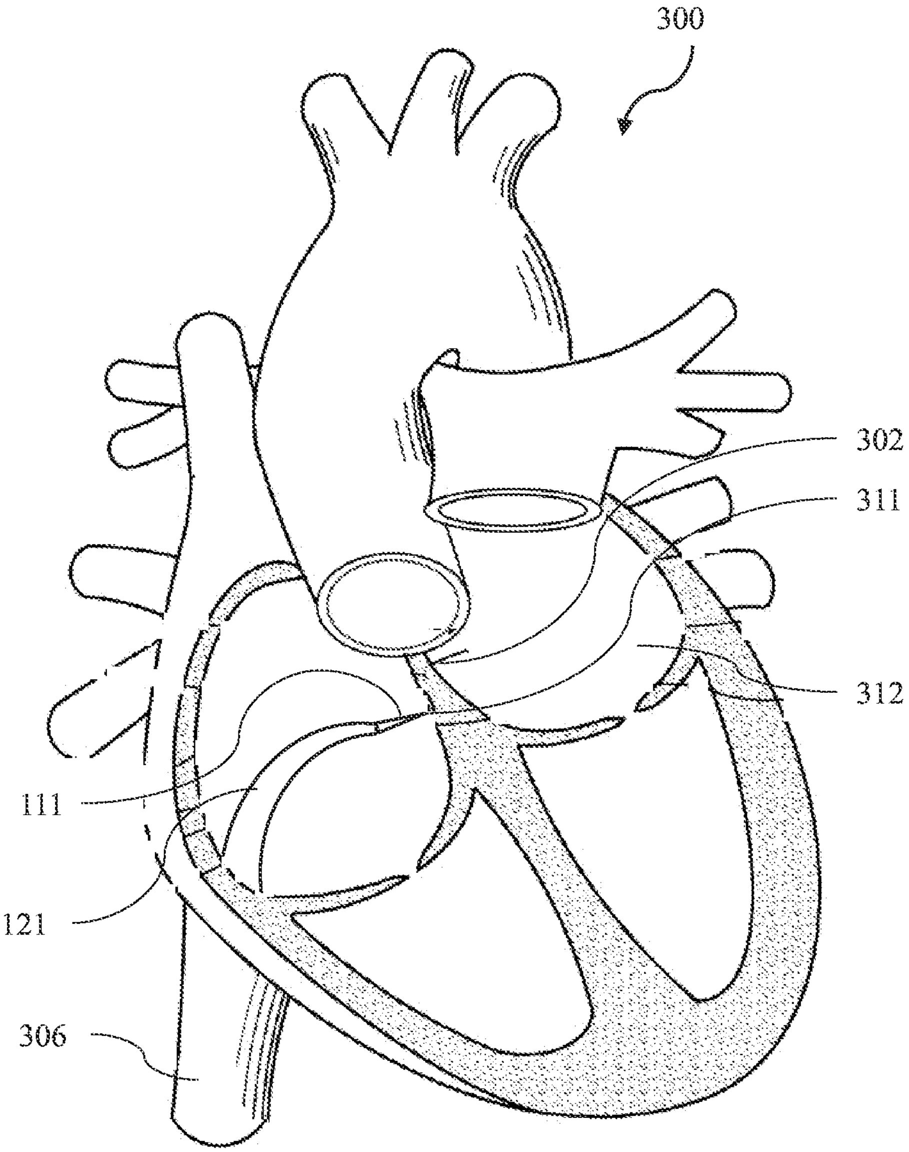

As shown in FIG. 3B, in order to deliver the operative distal tip of the dilator against the atrial septum 302, a dilator 120 with at least one lumen 127 sufficient to accommodate the outer diameter of the flexible wire 110 may be introduced into the patient's vasculature. The dilator 120 is advanced along the flexible wire 110 into position 311 adjacent a region of the septum 302 to be perforated. Alternatively, the flexible wire and dilator may be advanced together through the vasculature.

The support and etiology of the surrounding vasculature may aid in interpreting selection of a suitable perforation site. For example, according to one embodiment, a region of the interatrial septum that is situated above the sinotubular junction ("STJ"), may be selected to aid in eventual alignment of the flexible wire and steerable dilator when creating a perforation from the left atrium into the aorta.

The site of the transseptal perforation may be determined through suitable visualization methods, such as fluoroscopy through the use of RO markers on the dilator and/or flexible wire, electro-mechanical mapping for real-time placement of the flexible wire and dilator with targets predetermined by computerized tomography ("CT") scanning or in real-time, or through intracardiac echocardiography ("ICE") transesophageal echocardiography ("TEE") using appropriate markers on the flexible wire and/or the dilator. Contrast injection may also assist in visualization. Visualization may enable delineation of anatomy and optimal site targeting to avoid damaging the surrounding vasculature.

Once the position of the operative distal tip 111 of the flexible wire 110 is confirmed, the operative distal tip 111 is energized to create a perforation in the atrial septum 302. For example, if the flexible wire is an RF wire, then the flexible wire may be energized to deliver RF energy to perforate the target site. Alternatively, as described above, the perforation may be created using radiant, thermal or electrical energy as suitable for the selected type of flexible wire.

Figure 3C:
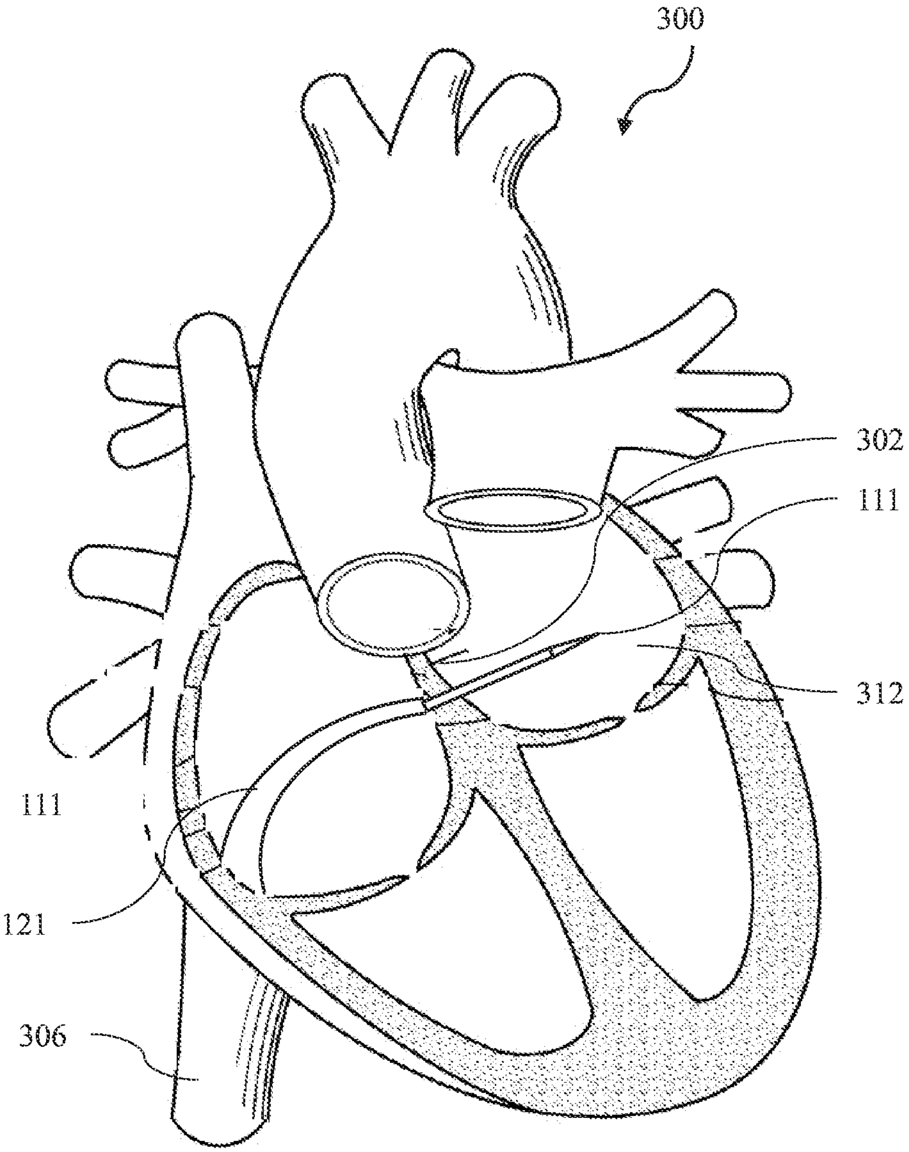

Referring to FIG. 3C, operative distal tip 111 of flexible wire 110 is thereafter advanced through the transseptal perforation at location 311 and into the left atrium 312. Advancement may be monitored using suitable visualization techniques, as previously described. Alternatively, advancement may be determined using a pressure sensor on the operative distal tip or distal section of the flexible wire to detect pressure differentials from the right atrium to the left atrium.

Figure 3D:
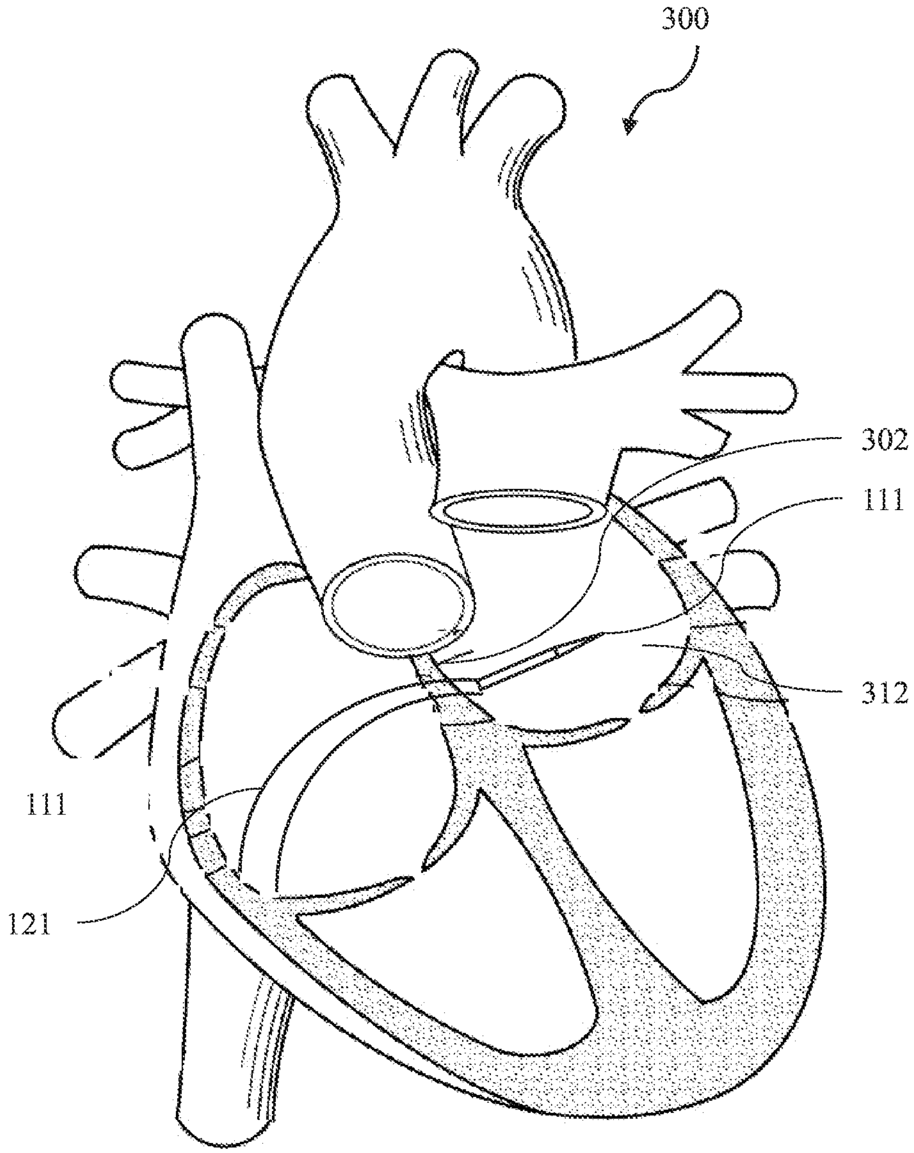

With the operative distal tip 111 of the flexible wire 110 situated within the left atrium 312, the dilator 120 is advanced along the flexible wire 110 into the left atrium 312, as shown in FIG. 3D. The dilator 120 may be advanced through the perforation by applying a longitudinal force to the proximal section of the dilator. If the heart 300 has been approached via the IVC, this longitudinal force may directly advance the dilator through the perforation. However, in some embodiments in which the heart has been approached via the SVC, applying a longitudinal force may push the dilator down along the septum rather than through the perforation. The dilator may be configured so that application of a longitudinal three onto a proximal section of the dilator may advance the distal section of the dilator through the perforation. For example, the dilator 120 may be shaped such that application of a longitudinal, downward force onto a proximal section of the dilator will cause a portion of the dilator to push against the free atrial wall. In turn this will transmit the longitudinal three in a lateral direction, thus forcing the tip 121 of the dilator 120 through the perforation. Alternatively, the dilator 120 may comprise a gentle curve which lends itself to transmitting mechanical force, such that the longitudinal force applied at a proximal section of the dilator will advance the distal section through the perforation. In such an embodiment, the flexible wire 110 may support the dilator 120 and prevent the dilator from slipping down the septum.

Figure 3E:
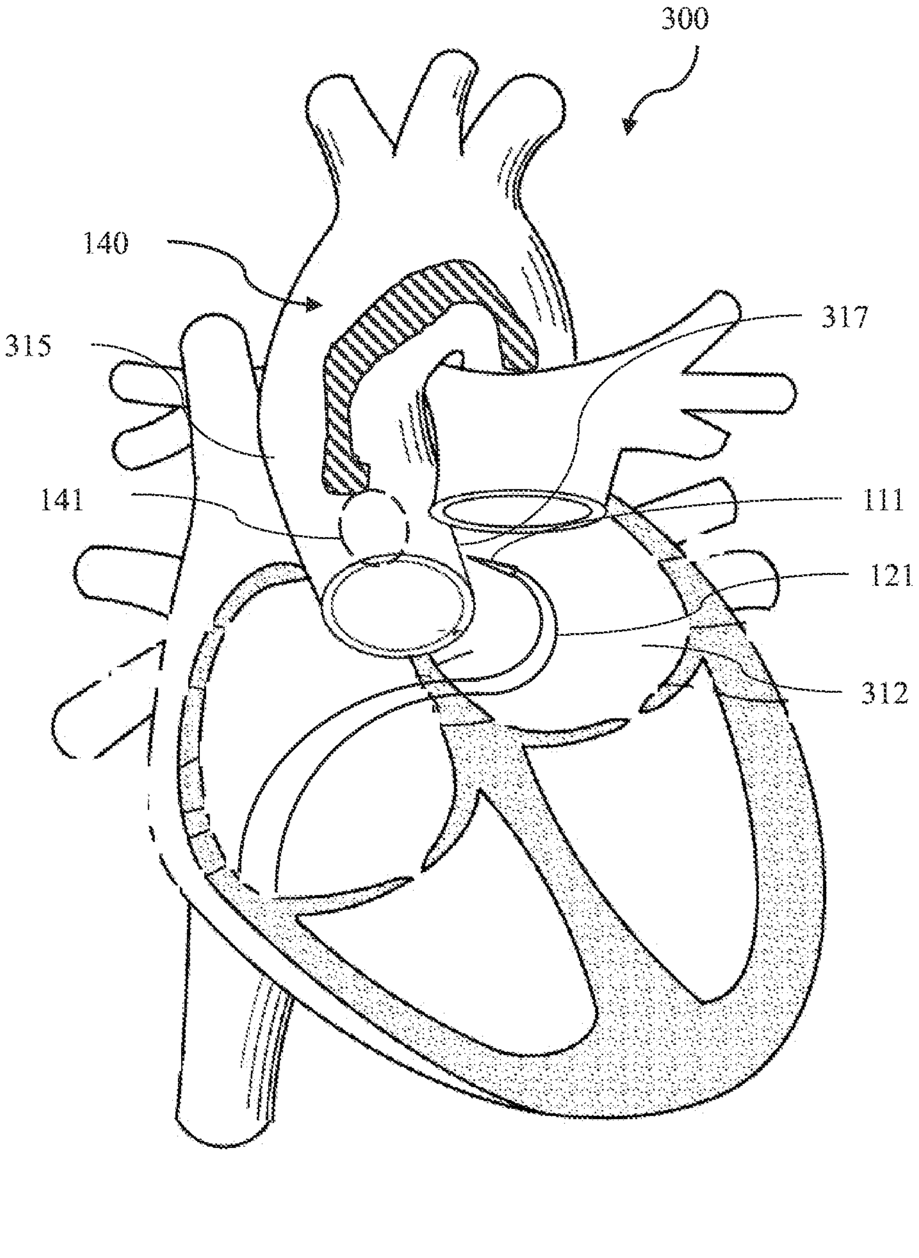

The dilator 120 is then advanced further along the flexible wire 110 until the dilator 120 is positioned at a target location 317 along the aorta 315, as shown in FIG. 3E.

In at least one embodiment, it may be advantageous to use the steerable dilator 110 to create a perforation between the aorta and the left atrium, while using a fixed curve dilator to create a perforation between the right atrium and the left atrium. For example, when creating a perforation from the aorta into the left atrium, it will be appreciated a more that a steerable dilator may be better suited to the more constrained approach available within the aorta than when approaching a perforation from within the left or right atrium. Accordingly, the steerable dilator may be withdrawn and exchanged with a fixed curve dilator, or a fixed curve dilator may be withdrawn and exchanged for the steerable dilator as suitable for the selected approach. The dilator used to position the flexible wire for creating the transseptal perforation may be withdrawn along the flexible wire 110 through the patient's vasculature and replaced with a different fixed dilator selected to achieve the target location 317 along the aorta 315

The curvature of a fixed curve dilator may be adjustable prior to insertion into a patient's vasculature, or it may be set to a certain curvature. For example, the dilator may have a metal shaft, such as a hypotube, disposed within at least a distal section of the fixed curve dilator to permit adjustment prior to introduction into the patient's vasculature. The metal shaft may extend along all or some of the length of the fixed curve dilator. The metal shaft may provide the fixed curve dilator with greater stiffness to facilitate transmission of a force applied to a proximal section along the length of the dilator to push the distal tip of the fixed curve dilator through perforations. Once the initial curvature of the fixed curve dilator is selected, the dilator is pushed through the patient's selected vasculature toward the patient's heart. The dilator navigates the vasculature as it progresses toward the heart. As the distal section of the fixed curve dilator enters the patient's heart, it resumes the initial curvature.

The position of the dilator may be observed using any suitable means, as previously described.

Figure 3F:
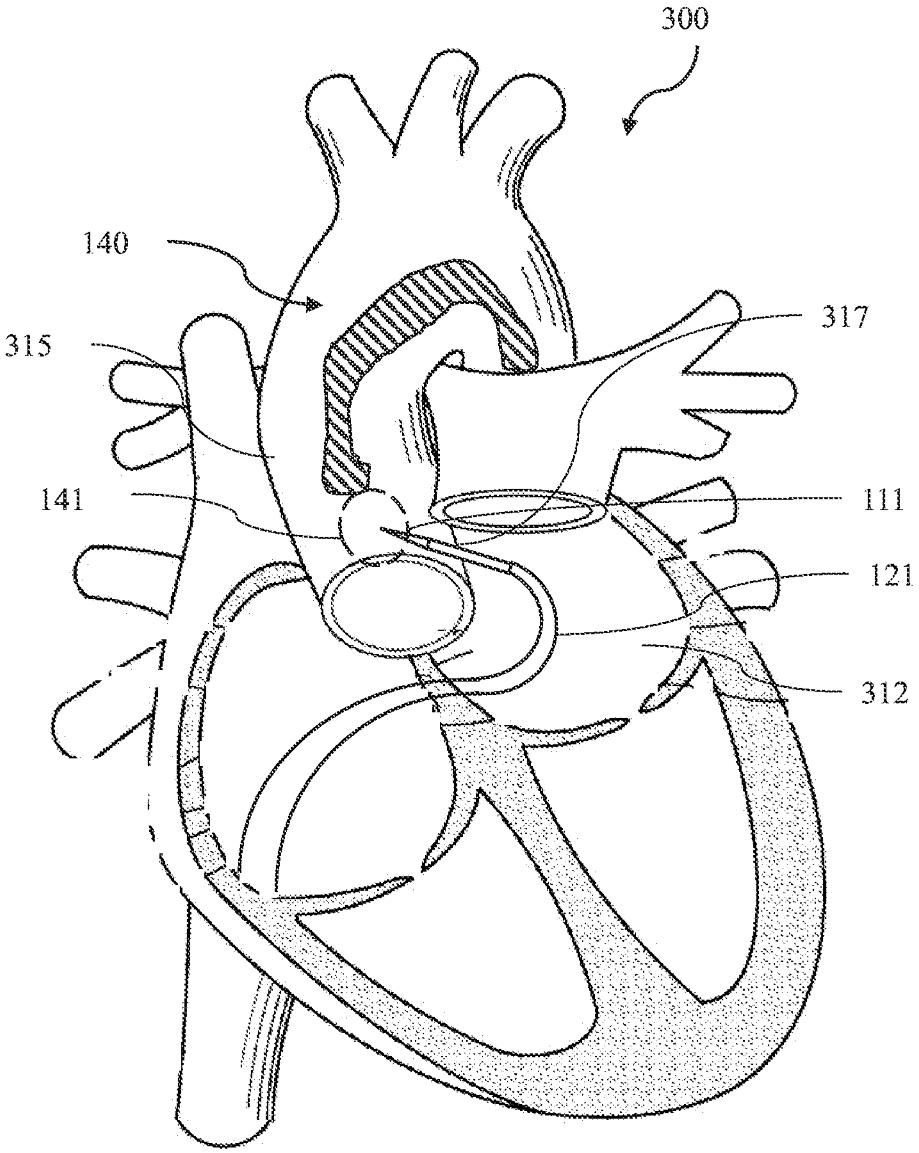

With the steerable dilator 120 adjacent the target location 317 along the aorta 315, the flexible wire 110 is energized to create a perforation from the left atrium into the aorta 315, as shown in FIG. 3F. Subsequently, the dilator 120 may be advanced further along the flexible wire 110 to enlarge the perforation, as shown in FIG. 3G, for example to support the delivery of a device such as an end-therapy device.

Access into the aorta 315 by the operative distal tip 111 of the flexible wire 110 and dilator 120 may be determined using suitable visualization or pressure sensing techniques as previously described.

Figure 3G:
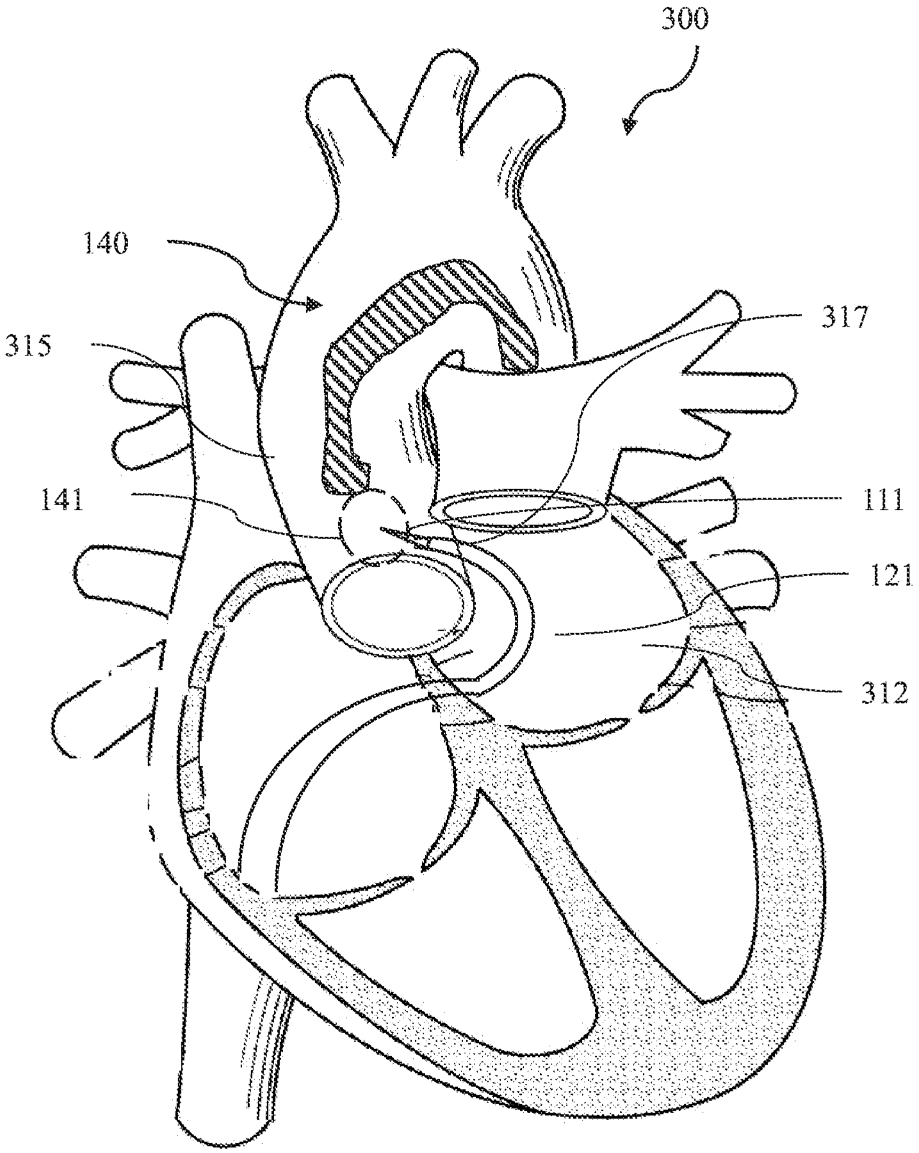
Figure 3H:
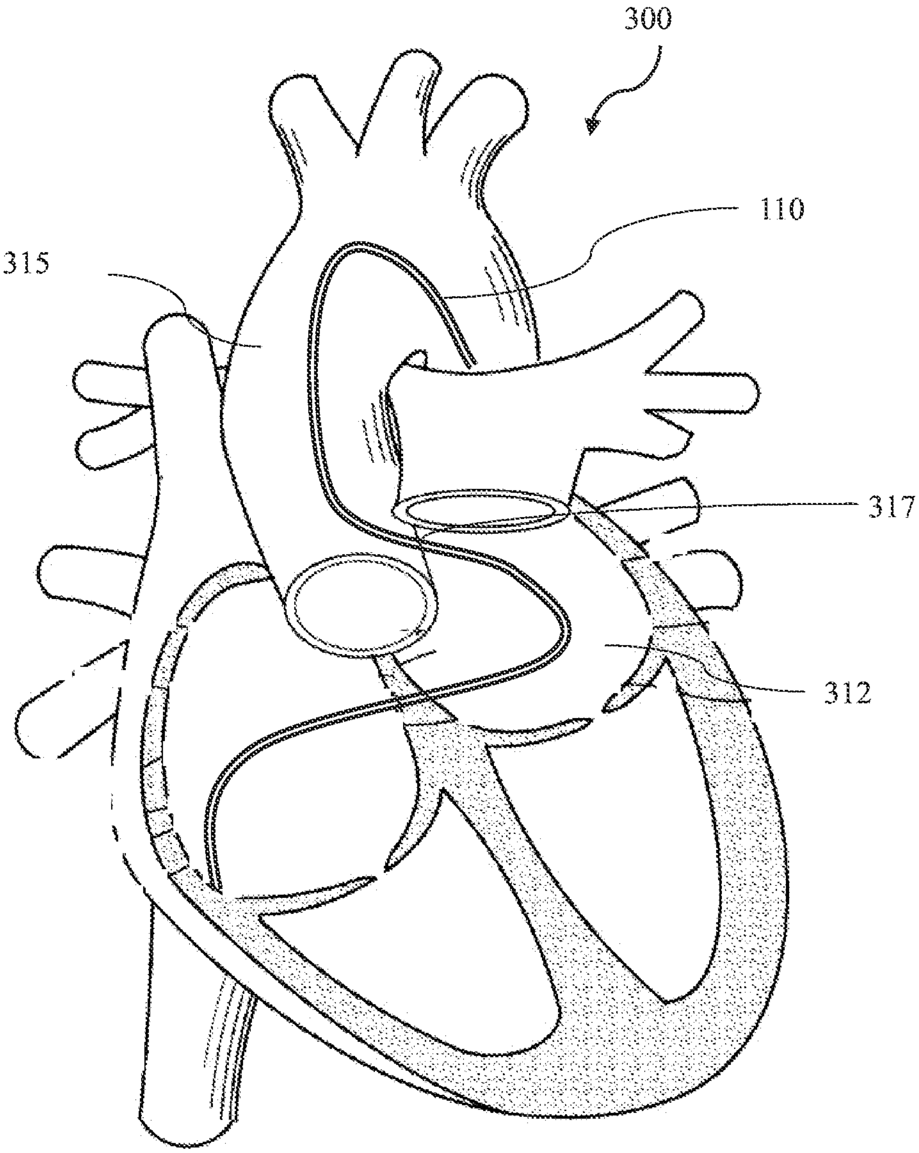

According to at least one embodiment, the dilator may be withdrawn from the patient's vasculature along the flexible wire 110, as shown in FIG. 3H.

According to one embodiment of this method, a lasso catheter 140 comprising a snare 141, or other suitable retaining device, is positioned in plane within the aorta so that, once the operative distal tip 111 of the flexible wire 110 enters the aorta 315, it proceeds into the snare 141 of the lasso catheter 140, as shown in FIGS. 3E to 3G. The lasso catheter 140 may be positioned peri-procedurally so that the snare 141 of the lasso catheter 140 is in plane when the flexible wire 110 enters the aorta 315, as shown. Once the operative distal tip 111 of the flexible wire 110 enters the snare 141, the lasso catheter 140 can be retracted to engage the operative distal tip 111 and draw the flexible wire 110 through the patient's vasculature, as shown in FIG. 3H. This may permit the flexible wire 110 to be flossed or replaced with a more rigid wire to facilitate placement of a selected device into position within the patient's heart 300. The lasso catheter may be positioned using visualization markers and techniques previously described with respect to the flexible wire and dilator.

In some embodiments, the flexible wire may be externalized to support advancement of end-therapy devices through the perforation between the aorta 315 and the left atrium 312. Externalization of the flexible wire 110 may be achieved through, for example, the patient's femoral artery, common carotids, or femoral vein. In at least one embodiment, access by a large-bore device through the perforation between the left atrium and the aorta may be achieved along the flexible wire 110 via the femoral artery or femoral vein. An externalized flexible wire having sufficient length may be used to support the introduction and positioning of stiffer therapeutic devices, such as end-therapy devices or end-therapy delivery devices.

According, to one embodiment, a left ventricular assist device is advanced along the flexible wire or a more rigid replacement into position between the left atrium 312 and the aorta 315 through the perforation enlarged by the dilator.

Figure 4A:
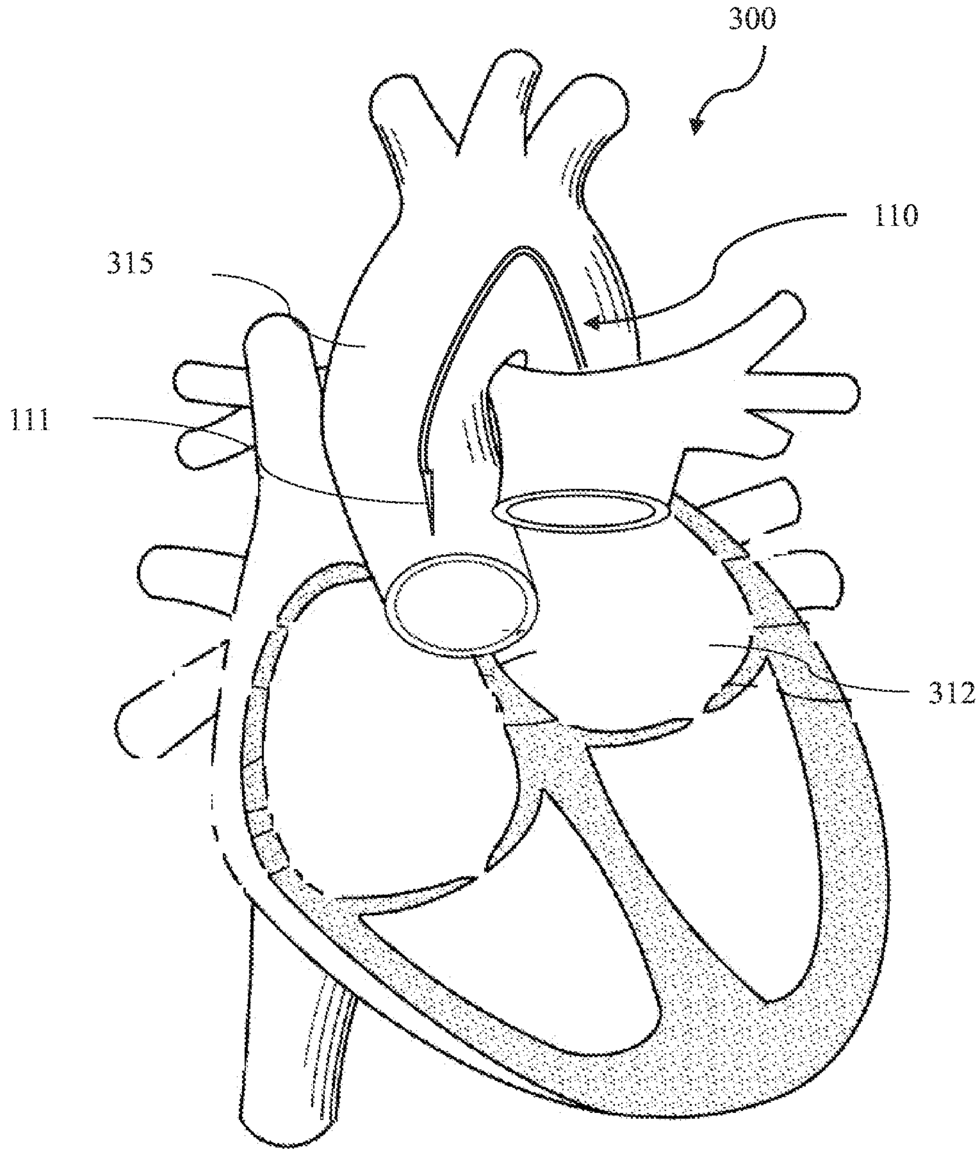
FIGS. 4A-4F illustrate an embodiment of a method to surgically create a perforation from the left atrium to the aorta of a patient's heart.

In another embodiment, a method for creating a perforation from the aorta to the left atrium is illustrated in FIGS. 4A to 4F. In accordance with a method aspect of this disclosure for creating a perforation from the aorta to the left atrium, the flexible wire 110 may be advanced into the ascending aorta 315, as shown in FIG. 4A. The flexible wire 110 may be introduced into the patient's vasculature to reach the ascending aorta 315 using suitable methods, such as Seldinger or Transcaval techniques, to gain arterial access via, for example, the left or right femoral artery and thence into the aorta 315.

Figure 2:
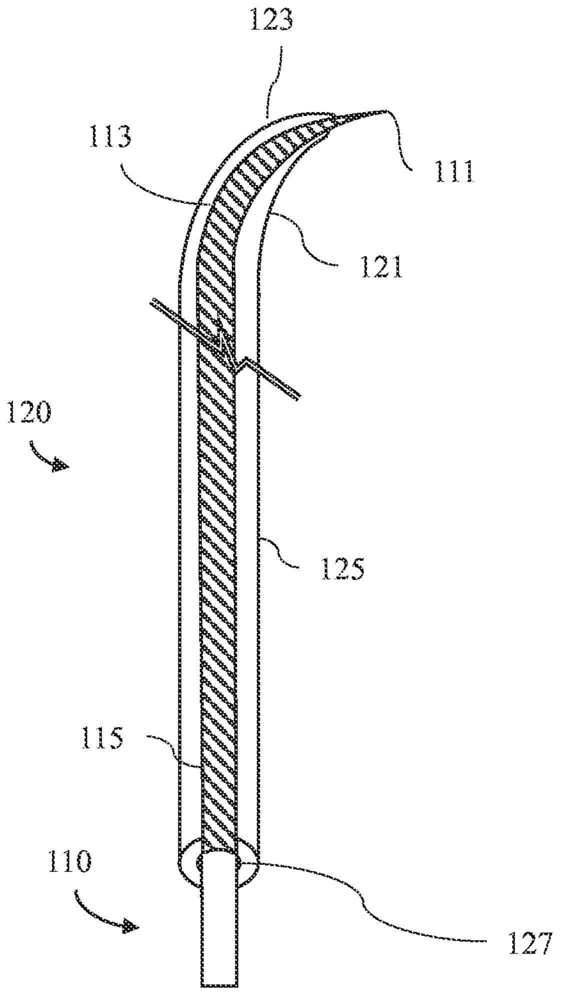
FIG. 2 is an illustration of a flexible wire within a dilator in accordance with an embodiment.
Figure 4B:
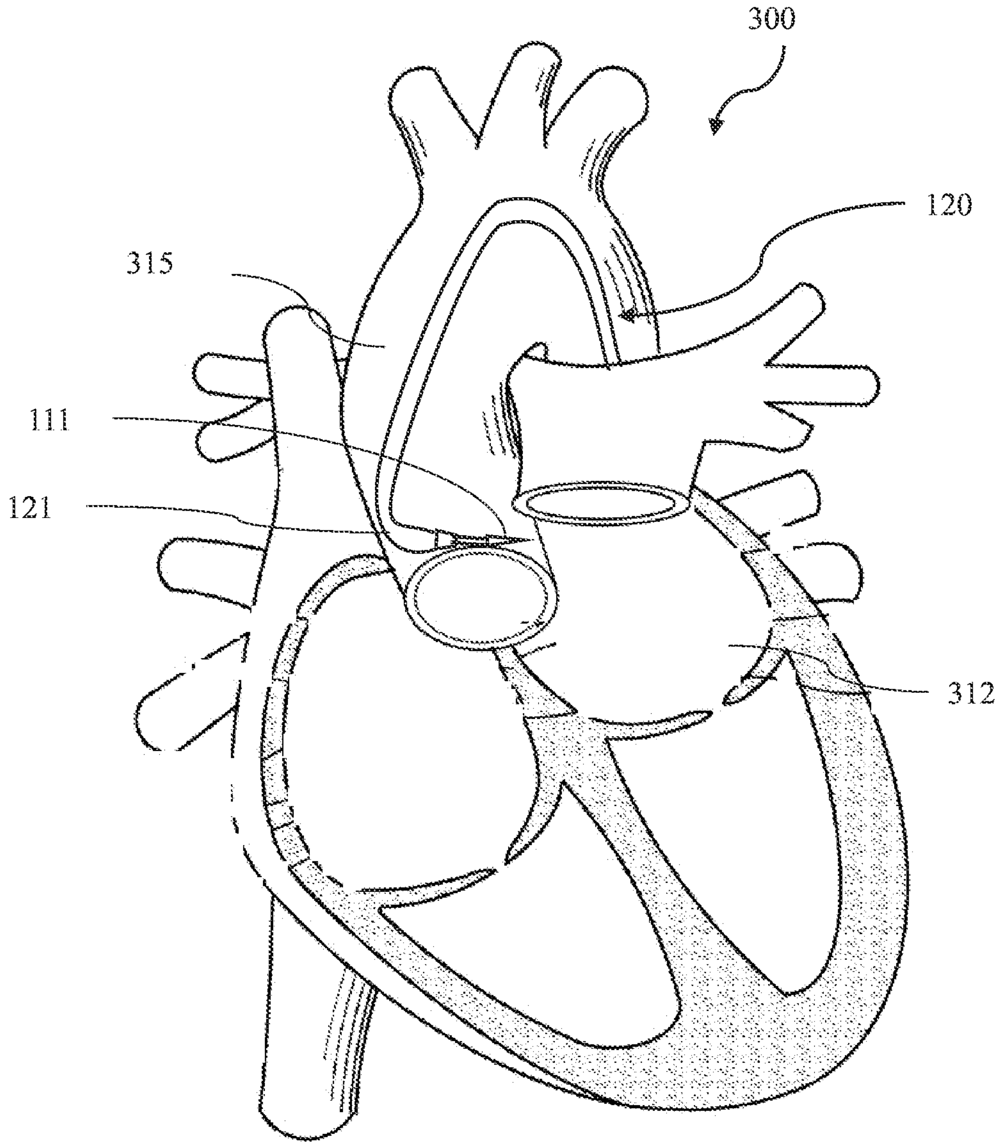

In order to deliver the operative distal tip 111 of the flexible wire 110 adjacent the target location 317 against the wall of the ascending aorta 315, a dilator 120 with at least one lumen 127 sufficient to accommodate the outer diameter of the flexible wire 110, as shown in FIGS. 1 and 2, may be introduced into the patient's vasculature. The dilator 120 is advanced along the flexible wire 110 into position 317 adjacent a region of the ascending aorta 315 to be perforated, as shown in FIG. 4B. Alternatively, the flexible wire and dilator may be advanced together through the vasculature.

The target location 317 of the of the desired perforation may be determined through suitable visualization methods as previously described.

Once the position of the operative distal tip 111 of the flexible wire is confirmed, the operative distal tip is energized to create a perforation in the wall of the ascending aorta 315 into the left atrium 312. For example, a generator may be activated and RE energy delivered to the operative distal tip 111 to create the perforation. Alternatively, as described above, the perforation may be created using radiant (e.g., laser), thermal or mechanical energy.

Figure 4C:
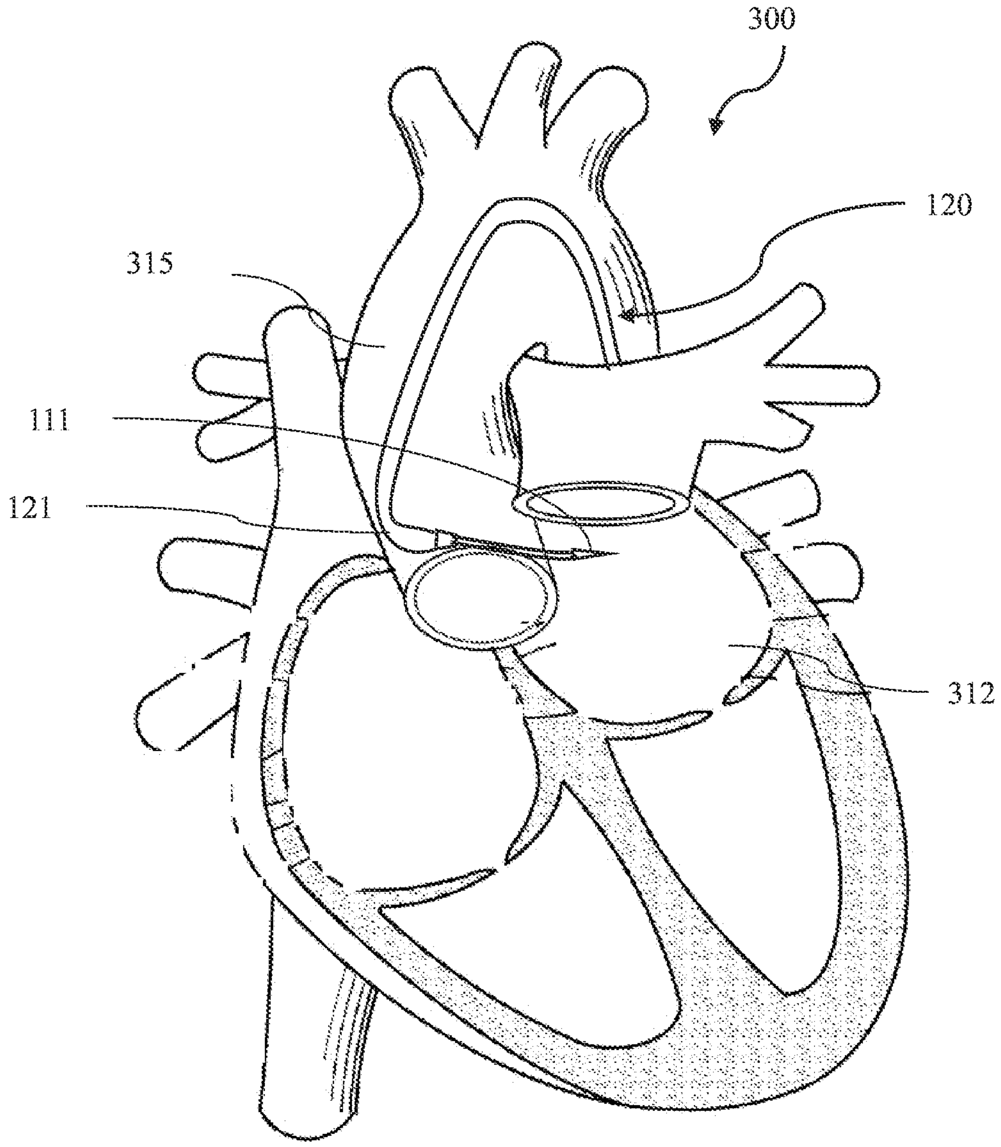

Referring to FIG. 4C, operative distal tip 111 of flexible wire 110 continues through the perforation and into the left atrium. Advancement may be monitored using, for example, fluoroscopy with radiopaque markings on the distal section 113 of flexible wire 110.

Figure 4D:
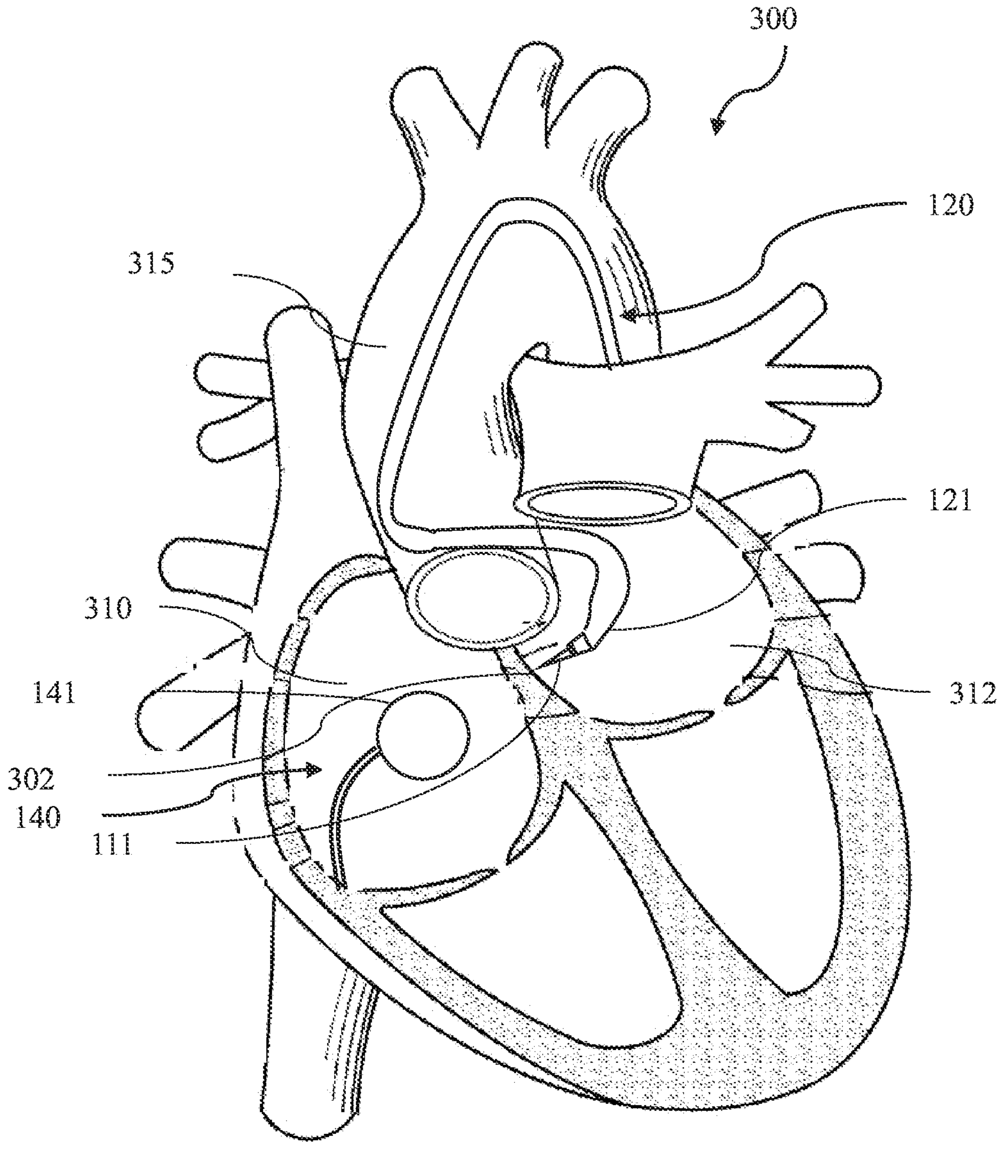

With the operative distal tip of the flexible wire 110 situated within the left atrium 312, the dilator 120 is advanced along the flexible wire 110 into the left atrium 312 to expand the perforation. The dilator 120 continues to be advanced along the flexible wire 110 until it positions the operative distal tip 111 adjacent a suitable location 331 along the septum 302, as shown in FIG. 4D.

In the illustrated embodiment, the same steerable dilator may be used to create the aorta to left atrium perforation and the transseptal perforation. Alternatively, as previously described, it may be advantageous to exchange a fixed curve dilator for the steerable dilator. Given the relatively tighter confines available when creating a perforation from inside the aorta 315 toward the left atrium 312 than when creating a perforation from the left atrium 312 toward the aorta 315, it will be appreciated that a steerable dilator is preferable for creating the perforation from the aorta to the left atrium. If desired, the steerable dilator may be withdrawn and exchanged for a fixed curve dilator to direct the flexible wire adjacent the desired location for the transseptal perforation.

The position of the dilator may be observed using any suitable visualization or pressure sensing techniques, as previously described.

Figure 4E:
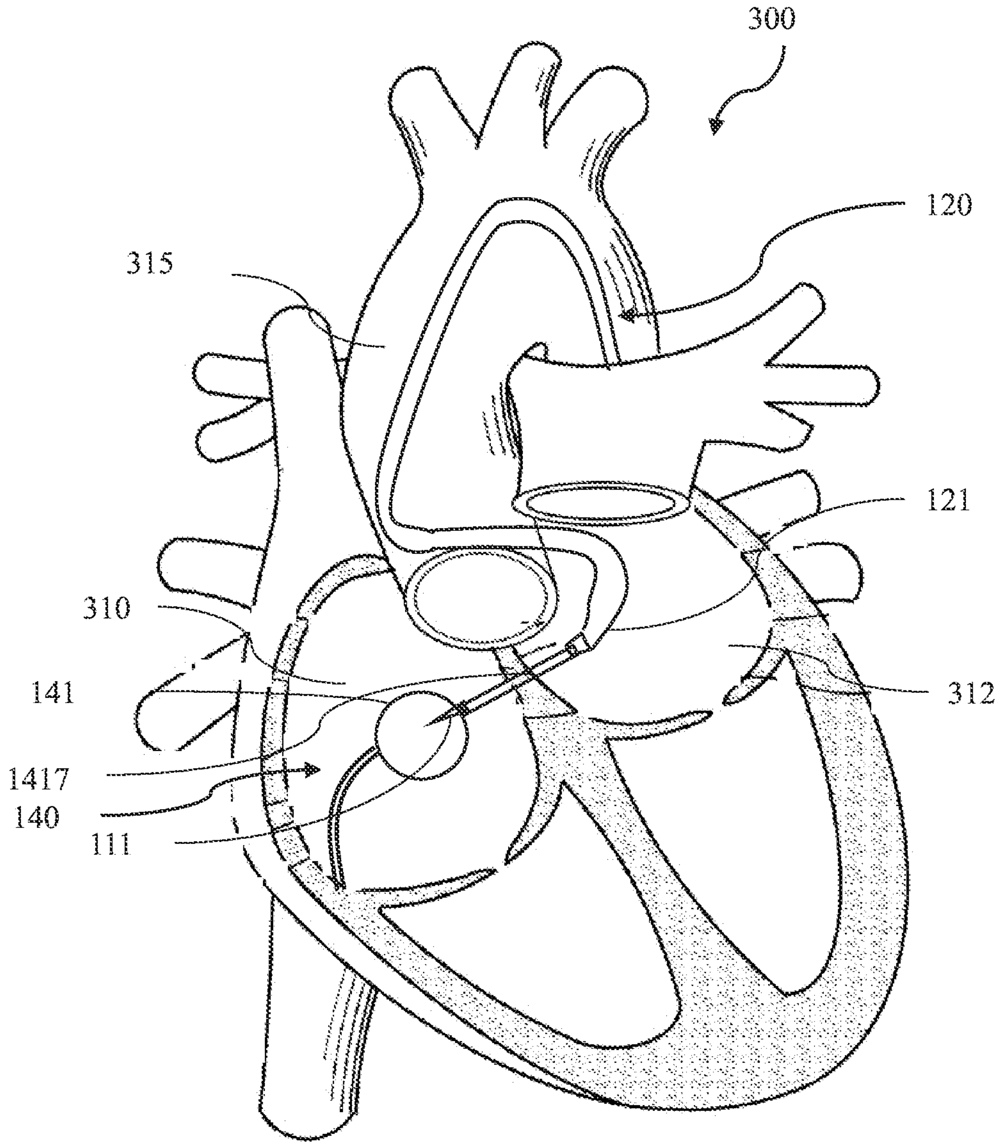

With the dilator 120 in position along the septum 302, the flexible wire 110 is energized to create a perforation from the left atrium 312 into the right atrium 310 at location 302. The operative distal tip 111 of flexible wire 110 is advanced into the right atrium 310, as shown in FIG. 4E. Subsequently, the dilator may be advanced further along the flexible wire to enlarge the perforation, as shown in FIG. 4F.

Access into the right atrium 310 by the operative distal tip 111 and dilator 120 may be determined via suitable visualization methods, as previously described.

According to at least one embodiment, the dilator may be withdrawn from the patient's vasculature.

Figure 4F:
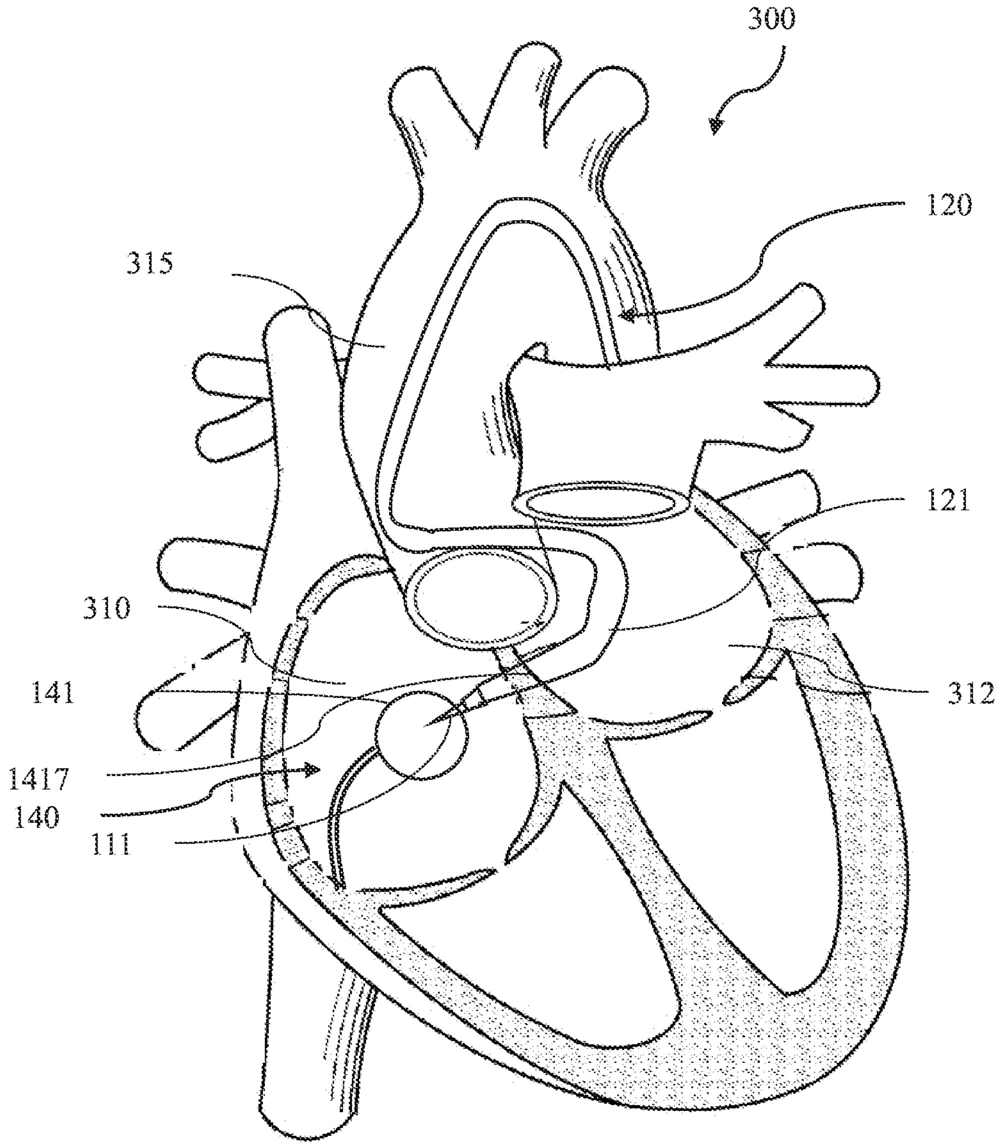

According to one embodiment of this method, a lasso catheter 140 comprising a snare 141, or other suitable retaining device, is positioned in plane within the right atrium 310 so that, once the operative distal tip 111 of the flexible wire 110 enters the right atrium 310, it proceeds into the snare 141 of the lasso catheter 140, as shown in FIGS. 4E to 4F. The lasso catheter 140 may be positioned periprocedurally so that the snare 141 of the lasso catheter 140 is already in plane when the operative distal tip 111 enters the right atrium 310, as in FIG. 4D. Once the operative distal tip 111 enters the snare 141, the lasso catheter 140 can be retracted to engage the operative distal tip and draw the flexible wire 110 through the patient's vasculature as shown in FIG. 3H, except using the approach according to this method. This may permit the flexible wire 110 to be flossed or replaced with a more rigid wire to facilitate placement of a selected device into position within the patient's heart.

In some embodiments, the flexible wire may be externalized to support advancement of end-therapy devices through the perforation between the aorta 315 and the left atrium 312. Externalization of the flexible wire 110 may be achieved through, for example, the patient's femoral artery, common carotids, or femoral vein. In at least one embodiment, access by a large-bore device through the perforation between the left atrium and the aorta may be achieved along the flexible wire 110 via the femoral artery or femoral vein.

According to one embodiment, a therapeutic device, such as an LVAD, is advanced along the flexible wire or a more rigid replacement from the right atrium, through the transseptal perforation into the left atrium 312 and into position between the left atrium 312 and the aorta 315 through the left atrium-aorta perforation enlarged by the dilator.

Figure 5:
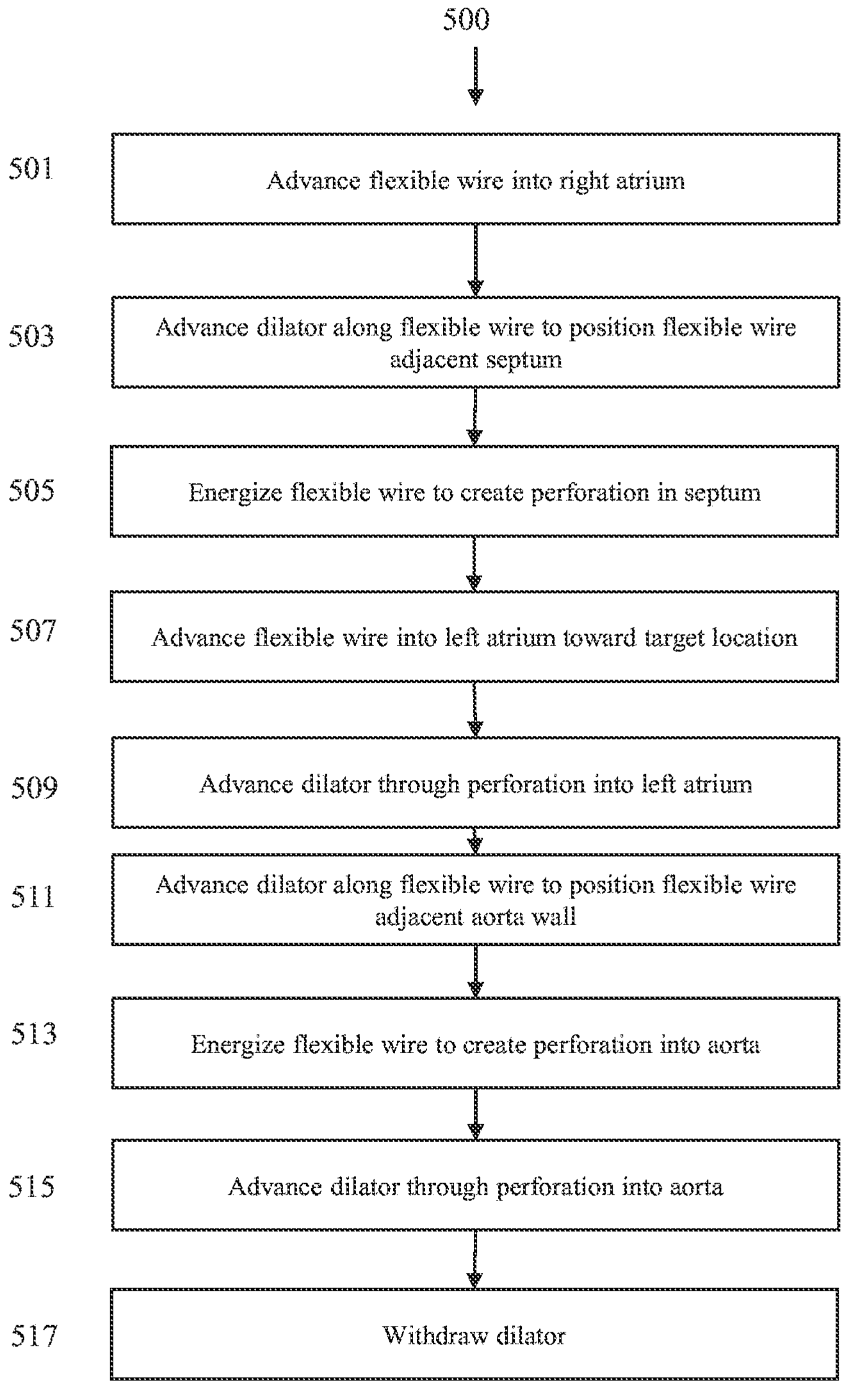
FIG. 5 illustrates a flow chart of an embodiment of a method to surgically create a perforation from the aorta to the left atrium of a patients heart.

Referring now to FIG. 5, operational steps of a method 500 for creating a perforation at a target location between an aorta and a left atrium of a patient's heart are outlined in flowchart form. The method 500 comprises: advancing a flexible wire into the right atrium of a patient's heart (step 501); advancing a dilator along the flexible wire to position the operative distal tip of the flexible wire adjacent a location of the septum to be perforated (step 503); energizing the flexible wire to create a perforation in the septum (step 505); advancing the flexible wire into the left atrium toward the target location (step 507); advancing the dilator along the flexible wire to direct the operative distal tip of the flexible wire adjacent the target location (step 509); energizing an operative distal tip of the flexible wire to create a second perforation at the target location (step 511); advancing the operative distal tip across the wall through the second perforation (step 513); advancing the dilator through the second perforation to enlarge the second perforation (515); and withdrawing the dilator from the heart (step 517).

Figure 6:
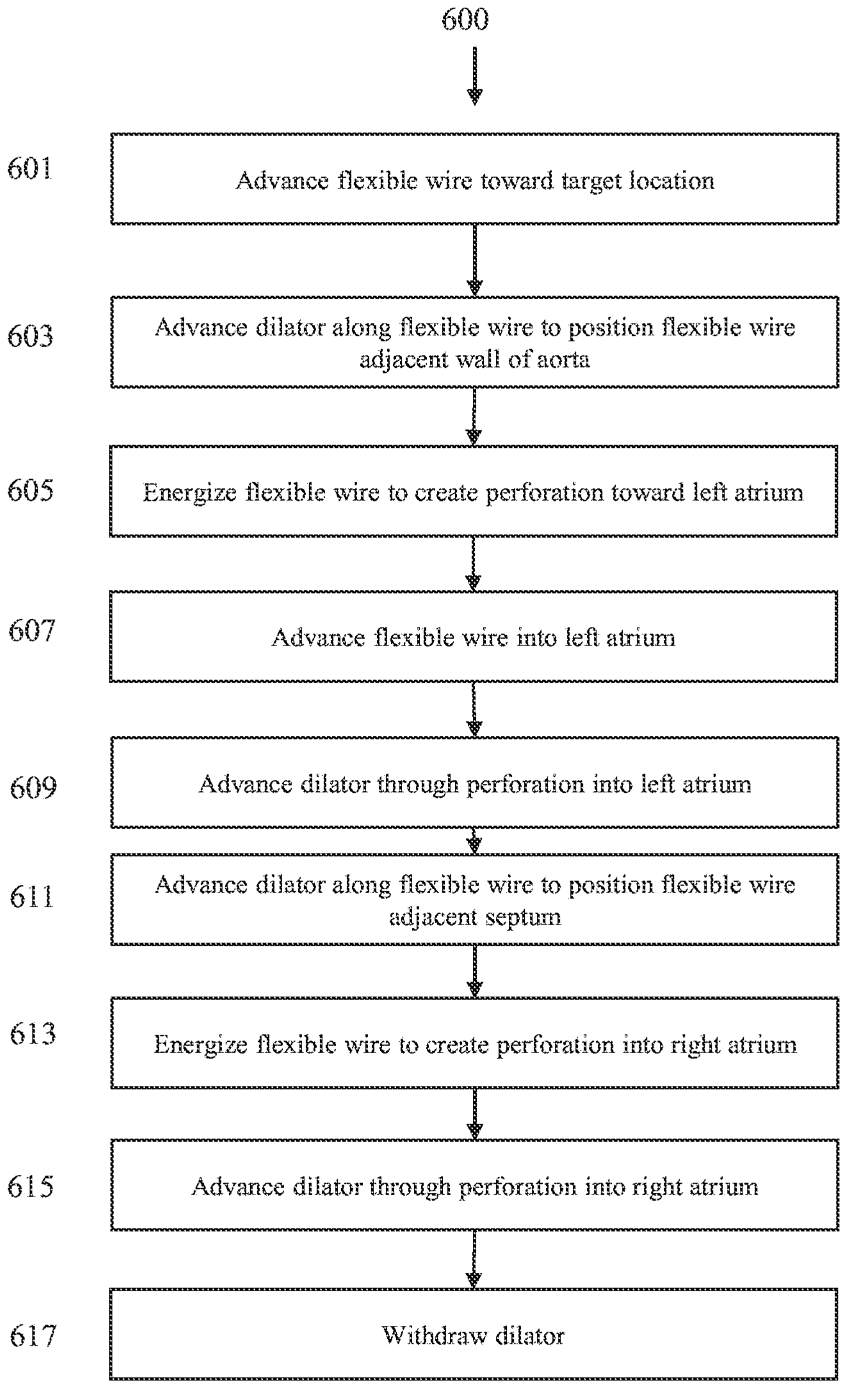
FIG. 6 illustrates a flow chart of an embodiment of a method to surgically create a perforation from the left atrium to the aorta of a patient's heart.

Referring now to FIG. 6, operational steps of a method 600 for creating a per at a target location between an aorta and a left atrium of a patient's heart are outlined in flowchart form. The method 600 comprises: advancing a flexible wire through the aorta toward the target location (step 601); advancing a dilator along the flexible wire to position the operative distal tip of the flexible wire adjacent the target location (step 603); energizing the flexible wire to create the perforation from the aorta to the left atrium (step 605); advancing the flexible wire into the left atrium (step 607); advancing the dilator along the flexible wire to direct the operative distal tip of the flexible wire adjacent a region of the septum to be perforated (step 609); energizing an operative distal tip of the flexible wire to create a second perforation from the left atrium to the right atrium (step 611); advancing the operative distal tip across the wall through the second perforation (step 613); advancing the dilator through the second perforation to enlarge the second perforation (615); and withdrawing the dilator from the heart (step 617).

As discussed above, it may be advantageous to employ a steerable dilator and a fixed curve dilator. For example, a fixed curve dilator having may be used to facilitate positioning of the flexible, wire adjacent the septum. Subsequently, a steerable dilator may be used to facilitate positioning of the wire adjacent the wall of the aorta. One embodiment may comprise two dilators which may be exchanged during the course of the procedure. In other words, one dilator may be used to position the flexible wire for perforation of the septum and, after perforation of the septum, the dilator may be exchanged for another dilator to position the flexible wire for perforation of the aorta. Conversely, a first dilator may be used to perforate the aorta toward the left atrium and, after perforation has been completed, the first dilator may be exchanged for a second dilator configured to position the flexible wire for perforating the atrial septum.

The present disclosure in various embodiments thus provides a system and method that is capable of creating a perforation by energizing a suitably positioned flexible wire. The energy may be selected from the group consisting of mechanical energy, electrical energy (various frequencies), radiant energy (e.g. laser) and thermal energy, amongst others. In at least one embodiment, the system may be provided as a kit comprising a flexible wire having an operative distal tip for creating a perforation in a patient's heart when energized, and a dilator configured to position the distal tip adjacent the target location and enlarge the perforation, and having at least one open lumen for receiving the flexible wire.

The present disclosure provides a method for the creation of a perforation in, for example, an atrial septum and between an aorta and a left atrium. Visualization techniques as disclosed herein are advantageous for positioning the flexible wire, dilator and lasso catheter within a patient's heart and for confirming that the operative distal tip of the flexible wire has entered into the aorta, the left atrium or right atrium subsequent to perforation. Staining the atrial septum may also be advantageous in this procedure, as it easily identifies the region of the atrial septum (fossa ovalis) to be perforated. It should be noted, however, that a method of the present invention may be practised without any or all of pressure monitoring or visualization and is thus intended to comprise a method of creating a perforation in a tissue utilizing any intravascular approach.

The present disclosure also provides a method for delivering the dilator over the flexible wire into the left atrium, right atrium or aorta once a successful perforation has been created. Once again, in order to successfully advance the dilator through the perforation, it may be advantageous to employ devices with appropriate shapes and configurations, as has been described.

One of the motivations for creating a perforation between the aorta and left atrium is to deliver treatment or monitoring devices, such as LVADs. An application of a method aspect of the present invention may involve the implantation of a device, such as an LVAD in communication between aorta and the left atrium of a patient's heart. In one embodiment, the device may be used during a desired period and may then be removed, without being permanently implanted into the patient. The present system and method may also facilitate the study or placement of end-therapy devices.

In alternative embodiments, the methods of the present disclosure may be used to create a perforation between the aorta and the left atrium to position a stent or a pressure-sensitive catheter through the perforation and between the left atrium and the aorta.

In at least one embodiment, the method and system of the present disclosure may be used to create large perforations between the atria and between the left atrium and aorta, as well as other perforations between other heart chambers and heart regions. All of these applications are intended to be exemplary only and are not intended to limit the scope of the present invention in any way.

The embodiments described in this disclosure are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The invention claimed is:

1. A method for creating a perforation at a target location between an aorta and a left atrium of a patient's heart, the method comprising:

- advancing an operative distal tip of a flexible wire into a right atrium of the patient's heart;
- advancing a steerable dilator along the flexible wire to position the operative distal tip adjacent a transatrial septum of the patient's heart, the steerable dilator comprising a steerable curvature that is adjusted to direct placement of the flexible wire within the patient's heart;
- energizing the operative distal tip to create a first perforation through the transatrial septum of the patient's heart;
- advancing the operative distal tip into the left atrium of the patient's heart;
- advancing the steerable dilator through the first perforation into the left atrium of the patient's heart;
- advancing the steerable dilator to position the operative distal tip at the target location within the left atrium of the patient's heart;

positioning a lasso catheter in plane within the aorta of the patient's heart at the target location;

energizing the operative distal tip to create the perforation at the target location;

advancing the operative distal tip through the perforation at the target location and into the aorta;

engaging the operative distal tip with the lasso catheter; and advancing the steerable dilator through the perforation at the target location to enlarge the perforation at the target location.

2. The method of claim 1, wherein the lasso catheter is positioned in plane within the aorta such that the operative distal tip exits through the perforation at the target location into the aorta through a snare of the lasso catheter.

3. The method of claim 2, further comprising flossing the flexible wire after the lasso catheter engages the operative distal tip.

4. The method of claim 3, wherein positioning the operative distal tip at the target location comprises adjusting the steerable curvature of the steerable dilator to achieve alignment above a sinotubular junction prior to the perforation at the target location.

5. The method of claim 1, wherein access to the target location is through the patient's vasculature.

6. The method of claim 1, wherein the operative distal tip is energized using any of radio-frequency energy, mechanical energy, electrical energy, radiant energy and thermal energy.

7. The method of claim 1, further comprising:

advancing a therapeutic device along the flexible wire through the perforation at the target location between the left atrium and the aorta.

8. The method of claim 7, wherein the therapeutic device comprises a left ventricular assist device.

9. The method of claim 1, further comprising advancing a fixed curve dilator along the flexible wire to position the operative distal tip adjacent the transatrial septum prior to advancing the steerable dilator, and interchanging the fixed curve dilator with the steerable dilator subsequent to creation of the first perforation through the transatrial septum.

10. The method of claim 1, wherein the steerable dilator comprises a tapered tip configured to enlarge the perforation at the target location to accommodate advancement of a therapeutic device therethrough.

11. The method of claim 1, wherein the steerable dilator and the flexible wire each comprise visualization markers.

12. The method of claim 1, wherein the operative distal tip of the flexible wire is provided with an anchor to support the flexible wire in position after the perforation at the target location is created.

13. The method of claim 1 wherein the flexible wire is equipped with a pressure sensor for measuring at least one pressure gradient within the patient's heart.

* * * * *